United States Patent
Zheng et al.

(10) Patent No.: US 7,583,788 B2
(45) Date of Patent: Sep. 1, 2009

(54) MEASURING DEVICE FOR THE SHORTWAVELENGTH X RAY DIFFRACTION AND A METHOD THEREOF

(75) Inventors: Lin Zheng, Shiqiaopu (CN); Changguang He, Shiqiaopu (CN); Zhengkun Peng, Shiqiaopu (CN)

(73) Assignee: South West Technology & Engineering Institute of China, Chongqing (CN)

( * ) Notice: Subject to any disclaimer, the term of this patent is extended or adjusted under 35 U.S.C. 154(b) by 1 day.

(21) Appl. No.: 11/572,128

(22) PCT Filed: Jun. 30, 2005

(86) PCT No.: PCT/CN2005/000950

§ 371 (c)(1),
(2), (4) Date: May 22, 2007

(87) PCT Pub. No.: WO2006/005246

PCT Pub. Date: Jan. 19, 2006

(65) Prior Publication Data

US 2008/0095311 A1    Apr. 24, 2008

(30) Foreign Application Priority Data

Jul. 14, 2004    (CN)    .................... 2004 1 0068880

(51) Int. Cl.
*G01N 23/20*    (2006.01)

(52) U.S. Cl. ............................. 378/81; 378/72; 378/73; 378/79

(58) Field of Classification Search ............. 378/70–73, 378/75, 79, 81–83, 90
See application file for complete search history.

(56) References Cited

U.S. PATENT DOCUMENTS 3,527,942 A    9/1970    Roe et al.
3,903,415 A *  9/1975    Holzapfel .................... 378/75

(Continued)

FOREIGN PATENT DOCUMENTS

CN    2077546    5/1991

(Continued)

OTHER PUBLICATIONS

Automobile Technology Material, No. 5, 2002, Li runshe et al. "Modification of automatic control and data processing system of X-ray stress instrument", pp. 27-30, all document.

(Continued)

*Primary Examiner*—Edward J Glick
*Assistant Examiner*—Thomas R Artman
(74) *Attorney, Agent, or Firm*—Lackenbach Siegel, LLP; Andrew F. Young

(57) ABSTRACT

A measuring device for the short-wavelength X-ray diffraction for test samples or work pieces made of lower-atomic-number crystalline and a method thereof are disclosed in the present invention. The measuring device comprises: an X-ray tube, an incident diaphragm, a table, a position-restricting receiving slit for a position-restricted part of a measured sample or work piece, a goniometer, a detector and an energy analyzer, the said X-ray tube and detector are arranged in the two sides of the table on which the sample or work pieces is located, the detector is intended to receive the transmitted diffracted ray. With the short-wavelength X-ray diffraction transmission method in the present invention X-ray diffracting patterns at different depths and different parts of a thicker test sample or work piece made of crystalline material and their distribution can be obtained without destructing the test sample or work piece, and then the data are processed by a computer to obtain phase, residual stress, etc. of any part and its distribution in the measured sample or work piece. The present invention has the advantages of easy operation, shorter detection time, and high trueness and reliability of the measured diffracting pattern.

44 Claims, 6 Drawing Sheets

U.S. PATENT DOCUMENTS

| | | | | |
|---|---|---|---|---|
| 5,259,013 | A | * 11/1993 | Kuriyama et al. | 378/43 |
| 5,459,770 | A | * 10/1995 | Salje | 378/71 |
| 5,949,811 | A | 9/1999 | Baba et al. | |
| 6,005,913 | A | * 12/1999 | Zombo et al. | 378/71 |
| 6,072,853 | A | * 6/2000 | Hall | 378/73 |
| 6,111,930 | A | 8/2000 | Schipper | |
| 6,307,917 | B1 | * 10/2001 | Shimizu et al. | 378/145 |
| 6,895,075 | B2 | * 5/2005 | Yokhin et al. | 378/90 |
| 2005/0058247 | A1 | * 3/2005 | Taguchi et al. | 378/71 |
| 2006/0176998 | A1 | * 8/2006 | Korsunsky | 378/71 |

FOREIGN PATENT DOCUMENTS

| | | |
|---|---|---|
| CN | 1137368 | 12/1996 |
| CN | 1038874 | 6/1998 |
| CN | 1049496 | 2/2000 |
| CN | 1291720 | 4/2001 |
| CN | 2496018 Y | 6/2002 |
| CN | 1504744 | 6/2004 |
| DE | 1598413 | 4/1970 |
| GB | 2228167 A | 8/1990 |
| GB | 2228167 A * | 8/1990 |
| JP | 03291555 A * | 12/1991 |
| JP | 11267120 | 5/1999 |
| JP | 2001095789 | 4/2001 |
| WO | WO 00/36405 | 6/2000 |
| WO | WO 03/060497 | 7/2003 |

OTHER PUBLICATIONS

International Search Report, PCT/CN2005/000950, Sep. 22, 2005, 11 pages.

Journal of the Chinese Ceramic Society, entitled, "Study of Chemical Reaction Between Polyvinyl Alcohol and Titanate Coupling Agent by X-Ray Photoelectron Spectroscopy", dated Aug. 2001, vol. 29, No. 4, pp. 1-5. (English Abstract).

International Search Report, PCT/EP03/00451, Mar. 3, 2003, pp. 1-3 (English).

* cited by examiner

MEASURING DEVICE FOR THE SHORTWAVELENGTH X RAY DIFFRACTION AND A METHOD THEREOF

STATEMENT OF PRIORITY AND CROSS REFERENCE

This application claims priority to International App. Ser. No. PCT/CN2005/000950 filed Jun. 30, 3005, which in turn claims priority to Chinese App. Ser. No. 200410068880.2 filed Jul. 14, 2004, the contents of each of which are enclosed herein by reference.

FIELD OF THE INVENTION

The invention relates to X-ray diffraction measurement, especially a short-wavelength X-ray diffraction scan measuring device and the method thereof for test samples or work pieces made of lower-atomic-number crystalline.

BACKGROUND OF THE INVENTION

Presently, X-ray diffraction analysis for substances is widely used in many fields. For example, it can be used to measure structure of crystalline substances (e.g., phase analysis), structural changes of crystalline substances (e.g., residual stress measurement), etc. During X-ray diffraction analysis in the prior art, an X-ray tube with a material Cu, Cr, Fe, or Mo as the anode target are often used. However, the characteristic X-ray emitted from such an X-ray tube is of long wavelength and therefore can only achieve a depth of penetration not greater than $10^{-4}$ m in some materials such as Mg, Al, or Si. As a result, X-ray diffraction analysis is only applicable to the surface of a test sample or work piece made of such a material, up to the present.

In view of the drawback that the penetration capability of X-ray is not so strong due to a long X-ray wavelength, patent CN1049496C discloses an "X-Ray Residual Stress Measuring Device and Method"; wherein, the device in that patent employs a X-ray tube emitting a short-wavelength characteristic X-ray and high tube voltage modified based on that of an existing X-ray residual stress measuring device, and the receiving slit is a position-restricting receiving slit that only receives diffracted rays from a measured part in a test sample or work piece. In the X-ray diffraction measuring method disclosed in the patent, short-wavelength characteristic X-rays are employed based on a measuring method for the existing device; the measured part is placed at the center of a goniometer circle, and only the diffracted rays from the measured part is permitted to enter into the radiation detector due to the position-restricting receiving slit, while the diffracted rays and scattered rays from any other part of the work piece are shielded, so that the residual stress at any part in the measured work piece can be measured within the range of penetration depth of the X-rays. By displacing the work piece, the X-ray stress analyzer can measure the residual stress at another part in the work piece; in that way, determination of three-dimensional distribution of residual stress in a work piece made of a material such as beryllium alloy is achieved. In addition, due to the fact that the shorter the X-ray wavelength is and the lower atomic number of one or more elements for the irradiated work piece materials is, the greater the penetration depth of the incident X-ray will be, diffracted rays from different depths and different positions in an even thicker work piece can be detected with such a method.

However, since the X-ray stress analyzer or the X-Ray Residual Stress Measuring Device employs an X-ray diffraction back reflection method to collect a diffraction pattern, the X-ray propagates over a longer path in the work piece. Furthermore, the intensity of the emergent ray from the work piece becomes more attenuated as the propagation path length increases, the principle being shown in FIG. 1, in which the intensity of an emergent ray corresponding to an incident X-ray with an intensity $I_0$ after passing through a work piece with a linear absorption coefficient $\alpha$ and a thickness t is $I=I_0 \times e^{-\alpha t}$. It can be seen from the above formula, the intensity of an emergent X-ray not only depends on the properties of the work piece and the intensity of the incident ray, but also varies with the propagation distance in the work piece; the longer the propagation distance is (i.e., the longer the sum of the propagation path lengths of the incident ray and diffracted ray in the work piece), the more the intensity loss will be, and thereby the lower the intensity of the emergent ray (the intensity of the diffracted ray) will be. A decreased intensity of the diffracted ray will cause a reduced SNR of measurement and thereby an adverse effect on the measurement of X-ray diffraction. As a result, the technique in the above patent cannot take full advantage of the strong penetration capability of a short-wavelength X-ray, resulting in a lower measurable depth inside of a measured work piece.

SUMMARY OF THE INVENTION

An object of the invention is to provide a scan measuring device for short-wavelength X-ray diffraction analysis mainly for lower-atomic-number crystalline test samples or work pieces made of Al, Mg, Si, etc., which can increase the measurable depth or thickness in work piece by about 10 times.

Another object of the invention is to provide an easy-to-operate and quick short-wavelength X-ray diffraction measuring method in which the above device is used.

It is common knowledge that the shorter X-ray wavelength is and the lower the atomic number of a radiated work piece substance is, the thicker the penetration of an incident X-ray in the work piece will be. Based on that principle, the invention employs an X-ray diffraction transmission method instead of an X-ray diffraction back reflection method, so as to reduce greatly the path length of an incident ray and diffracted ray in the work piece, and thereby reduces the intensity loss of the diffracted ray in the measured work piece, increases the intensity of the emergent ray, improves the SNR of the signals received by the detector, and improves the sensitivity of the entire diffraction measuring device. Therefore, diffracted X-rays from different depths and different positions in an even thicker work piece can be collected, so as to implement non-destructive X-ray diffraction analysis for the interior of the entire work piece, and obtain phase, stress, etc. at different depths and different positions in the work piece and their three-dimensional distributions.

An embodiment of the invention provides a short-wavelength X-ray diffraction measuring device, consisting of an X-ray tube, an entrance diaphragm, a table, a receiving slit, a goniometer, a detector, and an energy analyzer; wherein, the X-ray tube and the detector are located at the two sides of the table.

The receiving slit and detector are fixed to the goniometer and synchronously rotatable around a measured part of a work piece on the table. The measured part is located on a rotating axis of the goniometer. The goniometer is fixed on a platform. The table is fixed to the goniometer or the platform. The X-ray tube is fixed to the goniometer or the platform. The entrance diaphragm is fixed to the goniometer, the platform, or a clamp for the X-ray tube. An exit of the entrance diaphragm is located on or within the circumference of the goniometer. The work piece on the table can be displaced in X, Y, Z three dimensions along with the table, rotated to an angle Ψ around the rotating axis of the goniometer, or moved in X, Y, Z three dimensions and to an angle Ψ in a cooperative manner. In addition, the receiving slit in an embodiment of the invention also serves to permit only diffracted rays from the measured part of the work piece entering into the detector and shield scattered rays and diffracted rays from other parts of the work piece.

An anode target of the X-ray tube is made of a heavy metal material such as W, Au, or Ag, etc. so that it can emit a short-wavelength characteristic X-ray at 0.01 nm-0.07 nm wavelength with a strong penetration capability, which can penetrate to a depth at cm or dm level in a metal, non-metal, or ceramic material (e.g., Al, Mg, Si, etc.) with a low atomic number (Z<20). The tube voltage is 120-350 KV and the tube current is 2-10 mA, adjustable steplessly. The detector is a single-point radiation detector or a one-dimensional semiconductor detector array. The entrance diaphragm is a collimator entrance diaphragm. The receiving slit is a parallel position-restricting receiving slit or a tapered position-restricting receiving slit to shield scattered X-rays or diffracted rays from other parts of the work piece. The energy analyzer is a single-channel energy analyzer or a multi-channel energy analyzer, its input pulse signals come from the detector, with the output signals input to a computer. The table is controlled by a computer to be displaced in X, Y, Z three dimensions or rotated around the rotating axis of the goniometer.

The distance from the X-ray tube to the center of the goniometer circle is equal or not equal to the distance from the detector to the center of the goniometer circle, and is adjustable. The distance from the center of the goniometer circle to the radiation detector is 200-800 mm. The center of the goniometer circle in an embodiment of the invention is an intersection point between the rotating axis of the goniometer and the rotation plane of the radiation detector. An incident X-ray is in the rotation plane of the detector and passes through the center of the goniometer circle. A part of the work piece at the center of the goniometer circle is right a measured part.

The collimator entrance diaphragm is a round-aperture collimator entrance diaphragm or a rectangular-aperture collimator entrance diaphragm. A barrier material for the collimator entrance diaphragm is Pb or a heavy metal that has a stronger X-ray absorption capability than Pb, such as Au. If a single-point radiation detector, such as a scintillation counter, is used to scan and collect a diffraction pattern, the round-aperture collimator entrance diaphragm or rectangular-aperture collimator entrance diaphragm is used as a parallel position-restricting receiving slit, and the parallel position-restricting receiving slit and the radiation detector can be moved in a cooperative manner.

The round-aperture collimator entrance diaphragm is in an inner diameter of 0.1-2 mm and a length of 50-200 mm. The rectangular-aperture collimator entrance diaphragm is composed of two or more diaphragms, which are parallel to each other in the same direction and the center lines of which coincide with each other. The barrier material for each diaphragm is in a thickness of $\geqq 4$ mm. The spacing between the diaphragms is 20-200 mm. The inner aperture of each diaphragm is of $(1-4) \times (0.1-0.8)$ mm. The total thickness of the barrier materials for the entire rectangular-aperture collimator entrance diaphragm is not less than 15 mm.

The detector is packaged by a lead sheet in a thickness greater than 2 mm or another heavy metal sheet with a stronger X-ray absorption capability to shield X-rays, leaving only a window over against the receiving slit and a pinhole for leading out electric wires.

The one-dimensional semiconductor detector array is a positin sensitive detector in an embodiment of the present invention. The taper of the tapered position-restricting receiving slit depends on a limited angle detectable by the position-sensitive detector. A casing of the tapered position-restricting receiving slit is covered with a lead sheet in a thickness greater than 2 mm, and inlaid with 3-10 tungsten or molybdenum plates that divide the taper of the tapered position-restricting receiving slit evenly. The dimension of the larger opening of the slit matches the effective dimension of the position-sensitive detector, and the slit may be fixed to the position-sensitive detector. The tapered surface of the tapered position-restricting receiving slit intersects with the extension of the inlaid tungsten or molybdenum plates at the rotating axis of the goniometer. The tapered position-restricting receiving slit and the position-sensitive detector can be moved in a cooperative manner. If a position-sensitive detector is used to collect a diffraction pattern, a tapered position-restricting receiving slit is used as the receiving slit.

Another embodiment of the invention provides a short-wavelength X-ray diffraction measuring method for the above device, in which a short-wavelength X-ray diffraction transmission method is employed, including: (1) selecting radiation and diffraction test parameters, including tube voltage, tube current, diaphragm and slit system, energy analyzer, and the distance from the center of the goniometer circle to the radiation detector or position-sensitive detector, etc□(2) placing the measured part of the work piece at the center of the goniometer circle under the control of the computer; (3) measuring the diffraction pattern under the control of the computer; (4) moving the table in X, Y, Z three dimensions or rotating around the rotating axis of the goniometer as required under the control of the computer, so as to measure the diffraction pattern at any part in or any rotated angle of the work piece; (5) processing the data by the computer and obtaining the phase, residual stress parameters, and their distribution at the measured parts.

Selection of radiation and diffraction test parameters may be as follows: WKα, AuKα, or AgKα short-wavelength X radiation is selected; an X-ray diffraction and transmission method is chosen; a parallel position-restricting receiving slit or tapered position-restricting receiving slit is used to permit only diffracted rays from the measured part entering into the detector and shield the remaining rays.

The measured part of the work piece is placed at the center of the goniometer circle under the control of the computer; the measured part is any part on the surface of the work piece or inside of the work piece within a measurable thickness range.

During measurement of the diffraction pattern, the table on which the measured work piece is located can be moved in X, Y, Z three dimensions at a step length of 0.1-2 mm or rotated by any angle around the rotating axis of the goniometer as required under the control of the computer, so as to measure the diffraction pattern at any part in the work piece or the diffraction pattern at any rotated angle to that part around the rotating axis of the goniometer.

The device provided in the invention can measure an X-ray diffraction pattern at different depths and different positions in an even thicker test sample or work piece of crystalline material composed of one or more element with lower atomic number, such as Al, Mg, Si, C, N, or O, etc., without destructing the test sample or work piece of crystalline material. The invention breaks through the traditional concept that a short-wavelength X-ray is not applicable to the X-ray diffraction analysis field; it employs a method of short-wavelength X-ray radiation+X-ray diffraction transmission to improve the measurable thickness of a work piece by about 10 times compared with that by the device and method described in CN1049496C; especially for a work piece of a material such as Si, Al, Mg, etc., the measurable thickness can be up to cm to dm level. Therefore, the invention can be used to obtain an X-ray diffraction pattern at different depths and different positions in an even thicker work piece, and thereby obtain phase, residual stress, etc., and their distribution. Furthermore, the invention also breaks through the limit that the X-ray diffraction analysis is only applicable to a depth range of several tens of microns under the surface of a test sample with an existing X-ray diffractometer and method without destructing the test sample. In addition, the invention is advantageous for easy operation and short test time, and can obtain a true and reliable X-ray diffraction pattern.

Figure 1:
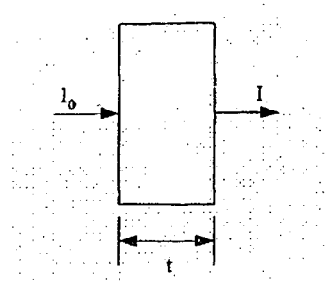
FIG. 1 is a schematic diagram of X-ray penetration through a substance.
Figure 2:
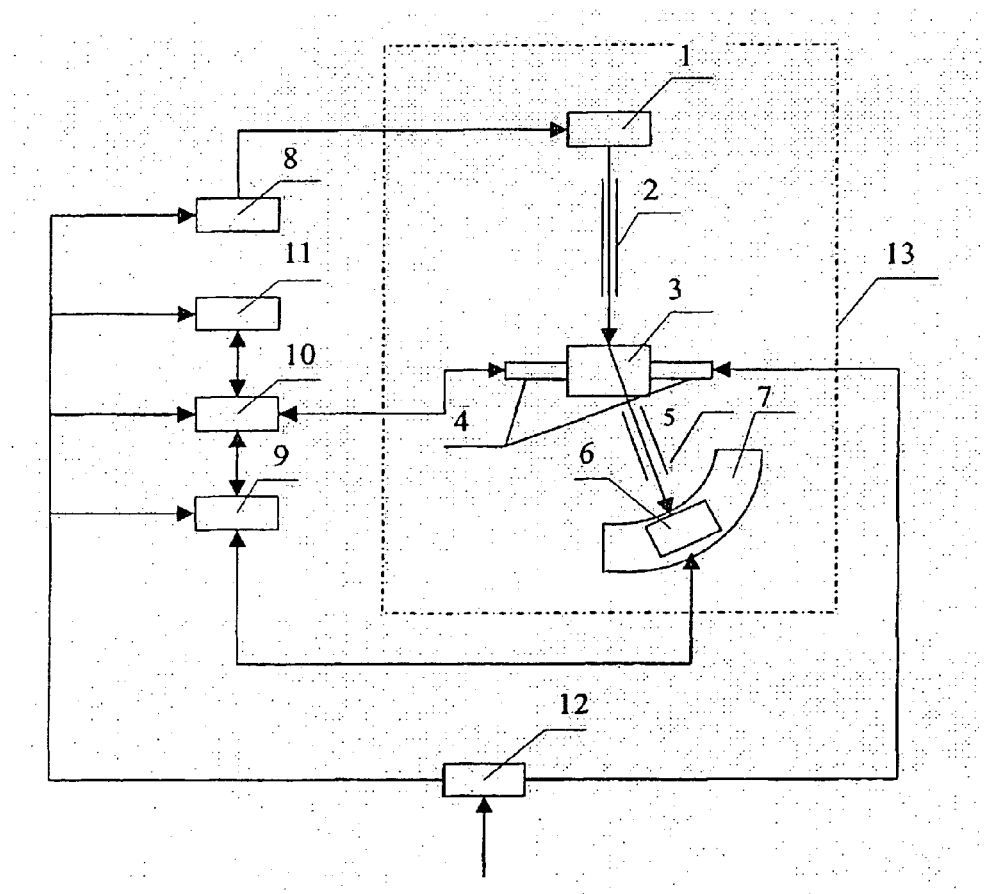
FIG. 2 is a block diagram of a device according to an embodiment of the invention.
Figure 3:
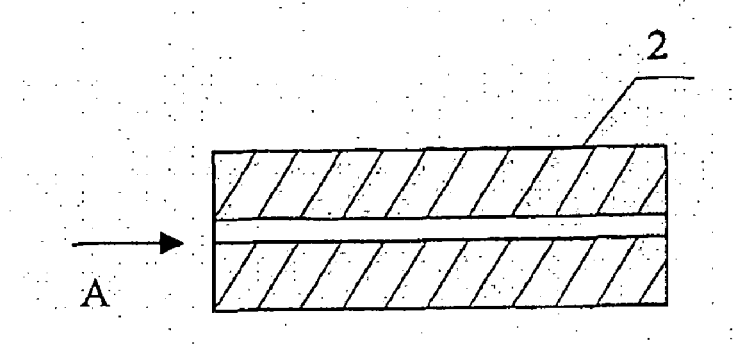
FIG. 3 is a sectional view of the structure of a round-aperture collimator entrance diaphragm according to an embodiment of the invention.
Figure 4:
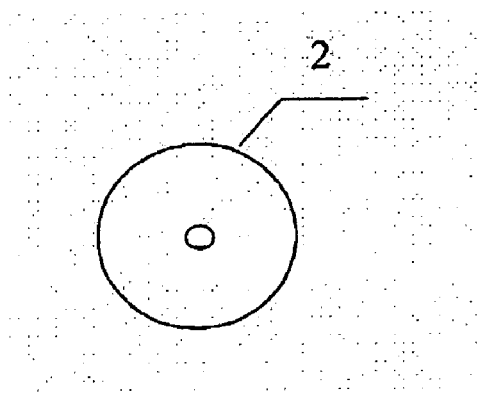
FIG. 4 is a view in direction A of FIG. 3.
Figure 5:
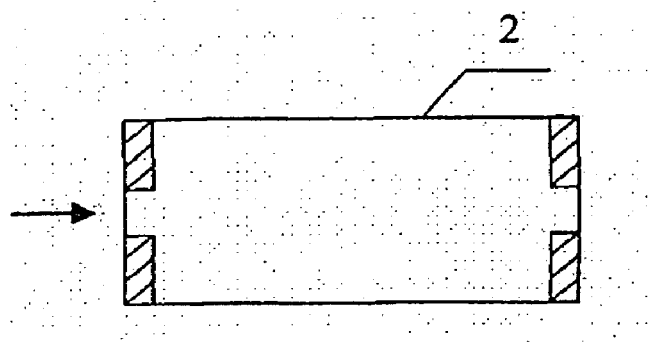
FIG. 5 is a sectional view of the structure of a rectangular-aperture collimator entrance diaphragm according to an embodiment of the invention.
Figure 6:
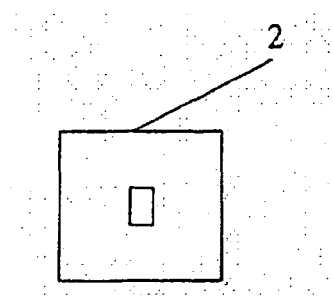
FIG. 6 is a view in direction A of FIG. 5.
Figure 7:
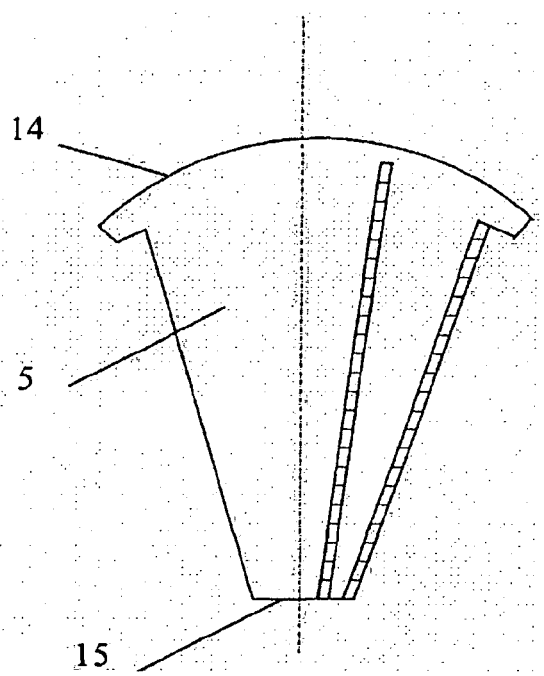
FIG. 7 is a sectional view of the structure of a tapered position-restricting receiving slit according to an embodiment of the invention, with a larger opening at the upper end 14 and a smaller opening at the lower end 15.
Figure 8:
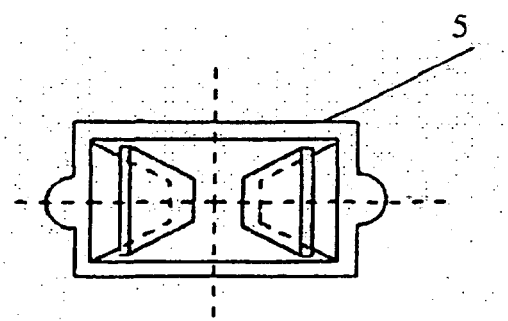
FIG. 8 is a top view of FIG. 7.

In the figures, 1 represents a X-ray tube; 2 a collimator entrance diaphragm; 3 a work piece; 4 a table; 5 a receiving slit; 6 a detector; 7 a goniometer; 8 a power source for an X-ray generator; 9 a energy analyzer; 10 a computer; 11 a data output unit; 12 a voltage stabilizer; 13 a platform for fixing the measuring device; 14 a larger opening at the upper end of a tapered position-restricting receiving slit; 15 a smaller opening at the lower end of the tapered position-restricting receiving slit.

DETAILED DESCRIPTION OF THE EMBODIMENTS

Hereunder the invention is described in detail in preferred embodiments, with reference to the attached drawings. First, it should be noted that the terms, words, and the meanings of the claims in this invention shall not be understood with their literal and ordinary meanings; instead, they also contain implications and concepts associated with the techniques provided in the invention, because, as the inventors, we have to provide appropriate definitions for the terms, so as to describe the invention in the most appropriate way. Therefore, the configurations described in embodiments of the invention and shown in the attached drawings are only preferred solutions instead of covering all technical features of the invention. It should be appreciated that there may be various equivalent or modified solutions to substitute those provided here.

In a first embodiment, as shown in the figures, a short-wavelength X-ray diffraction measuring device includes an X-ray tube 1, an entrance diaphragm 2, a table 4, a receiving slit 5, a goniometer 7, a detector 6, and an energy analyzer 9; wherein, the X-ray tube 1 and the detector 6 are located at the two sides of the table, i.e., at the two sides of a measured work piece.

The receiving slit 5 and the detector 6 are fixed to the goniometer 7 and can be rotated synchronously around a measured part of a work piece 3 on the table 4. The measured part is located on a rotating axis of the goniometer 7. The goniometer 7 is fixed to a platform 13. The table 4 is fixed to the goniometer 7 or the platform 13. The X-ray tube 1 is fixed to the goniometer 7 or the platform 13. The entrance diaphragm 2 is fixed to the goniometer 7, the platform 13, or a clamp for the X-ray tube 1; an exit of the diaphragm 2 is on or within the circumference of the goniometer 7. The measured work piece on the table 4 can be translated along with the table 4 in X, Y, Z three dimensions, rotated around the rotating axis of the goniometer 7 to an angle Ψ, or moved in X, Y, Z three dimensions and to an angle Ψ in a cooperative manner.

In an embodiment of the invention, an anode target of the X-ray tube 1 is made of a heavy metal material such as W, Au, or Ag. The tube voltage is 320 KV and the tube current is 5 mA, adjustable steplessly, so that the X-ray tube 1 can emit a short-wavelength characteristic X-ray at a wave length of 0.01 nm-0.07 nm with a strong penetration capability, which can penetrate to a depth of dm level in metal, non-metal, or ceramic material with a low atomic number (Z<20), such as Al, Mg, Si, etc. The detector 6 is a position-sensitive detector. The entrance diaphragm 2 is a collimator entrance diaphragm. The receiving slit 5 is a tapered position-restricting receiving slit for shielding scattered X-rays incident to the detector 6 and diffracted rays from any other part of the work piece, i.e., it only permits the diffracted rays from the measured part entering into the detector and shields the remaining rays. The energy analyzer 9 is a multi-channel energy analyzer. The table 4 can be translated in X, Y, Z three dimensions and rotated around the rotating axis of the goniometer 7 under the control of the computer 10. Signals from the multi-channel energy analyzer 9 are inputted to the computer 10.

The distance from the X-ray tube 1 to the center of the circle of the goniometer 7 is equal or not equal to the distance from the detector 6 to the center of the circle of the goniometer 7, and is adjustable. The distance from the center of the circle of the goniometer 7 to the radiation detector or position-sensitive detector is 600 mm.

The collimator entrance diaphragm is a round-aperture collimator entrance diaphragm or rectangular-aperture collimator entrance diaphragm. The barrier material for the collimator entrance diaphragm is Pb or a heavy metal with stronger X-ray absorption capability than Pb. If a single-point radiation detector, such as a scintillation counter, is used to scan and collect a diffraction pattern, a round-aperture collimator entrance diaphragm or rectangular-aperture collimator entrance diaphragm is used for the parallel position-restricting receiving slit.

The round-aperture collimator entrance diaphragm is in an inner diameter of 0.1-2 mm and a length of 50-200 mm. The rectangular-aperture collimator entrance diaphragm is composed of two or more diaphragms, which are parallel to each other in the same direction and the center lines of which coincide with each other. The barrier material for each diaphragm is in a thickness of 5 mm. The spacing between the diaphragms is 180 mm. The inner aperture of each diaphragm is of (1-4)×(0.1-0.8) mm. The total thickness of the barrier materials for the entire rectangular-aperture collimator entrance diaphragm is not less than 15 mm.

A lead sheet or a heavy metal sheet with a stronger X-ray absorption capability in a thickness greater than 2 mm is used for the radiation detector or position-sensitive detector to shield X-rays, leaving only a window over against the receiving slit 5 and a pinhole for leading out electric wires.

The taper of the tapered position-restricting receiving slit depends on a limited angle detectable by the position-sensitive detector. A casing of the tapered position-restricting receiving slit is covered with a lead sheet in a thickness greater than 2 mm, and lined with 3-10 tungsten or molybdenum plates that divide the taper of the tapered position-restricting receiving slit evenly. The dimension of a larger opening 14 of the slit matches the effective dimension of the position-sensitive detector, and the slit is fixed to the position-sensitive detector. The tapered surface of the tapered position-restricting receiving slit intersects with the extension of the lined tungsten or molybdenum plate at the rotating axis of the goniometer, wherein the center line of the tapered position-restricting receiving slit intersects with the center line of the lined tungsten or molybdenum plate at the center of the goniometer circle. The tapered position-restricting receiving slit and the position-sensitive detector can be moved in a cooperative way. If a position-sensitive detector is used to collect a diffraction pattern, a tapered position-restricting receiving slit is used as the receiving slit.

A short-wavelength X-ray diffraction measuring method for the above device, in which a short-wavelength X-ray diffraction and transmission method is employed, includes: (1) selecting radiation and diffraction test parameters, including tube voltage, tube current, diaphragm and slit system, and the distance from the center of the goniometer circle to the radiation detector or position-sensitive detector; (2) placing the measured part on the work piece at the center of the goniometer circle under the control of the computer; (3) measuring the diffraction pattern under the control of the computer; (4) moving the table in X, Y, Z three dimensions or rotating around the rotating axis of the goniometer as required under the control of the computer, so as to measure the diffraction pattern at any part in or at any rotated angle $\Psi$ of the work piece; (5) processing the data under the control of the computer and obtaining the phase, residual stress parameters, and their distribution at the measured parts.

Selection of radiation and diffraction test parameters may be as follows: WK$\alpha$, AuK$\alpha$, or AgK$\alpha$ short-wavelength X radiation is selected; an X-ray diffraction and transmission method is chosen; a parallel position-restricting receiving slit or tapered position-restricting receiving slit is used to permit only the diffracted rays from the measured part entering into the detector and shield the remaining rays.

Figure 9:
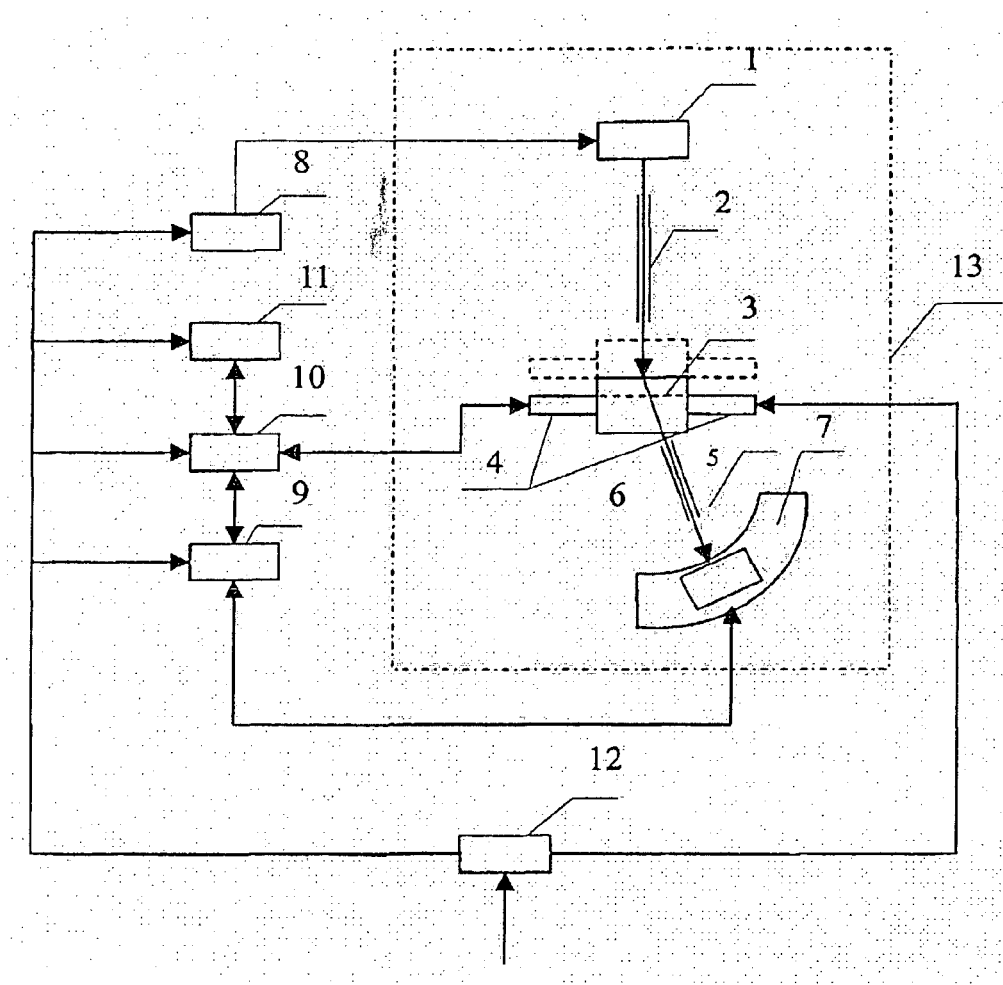
FIG. 9 is a schematic diagram of measurement with the work piece being moved according to an embodiment of the invention.
Figure 10:
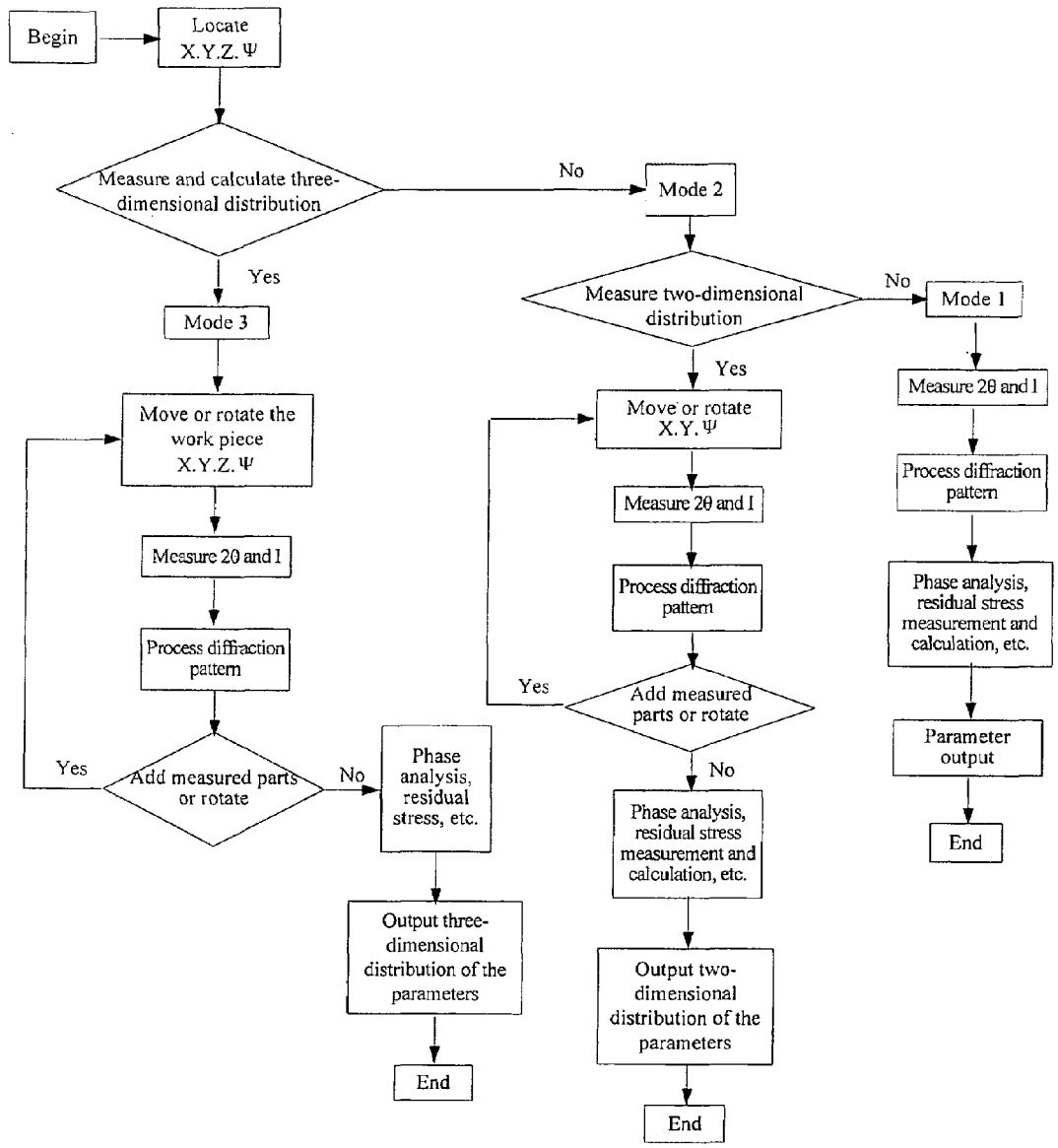
FIG. 10 is a block diagram of the measurement and calculation according to an embodiment of the invention.

The measured part of the work piece is placed at the center of the goniometer circle under the control of the computer; the measured part is any part inside of the work piece within a measurable thickness range. In order to implement part-by-part scan measurement, the measured work piece 3 on the table 4 shown in FIG. 9 is controlled by the computer to move in three dimensions at a step length of 0.1-2 mm. In order to measure a diffraction pattern for a measured part in any direction, the work piece 3 on the table 4 shown in FIG. 9 can be controlled by the computer to rotate to a certain angle around the rotating axis of the goniometer. The computer processes the obtained data and the output unit outputs the phase, residual stress parameters, and their distribution at individual parts in the measured work piece.

Figure 11:
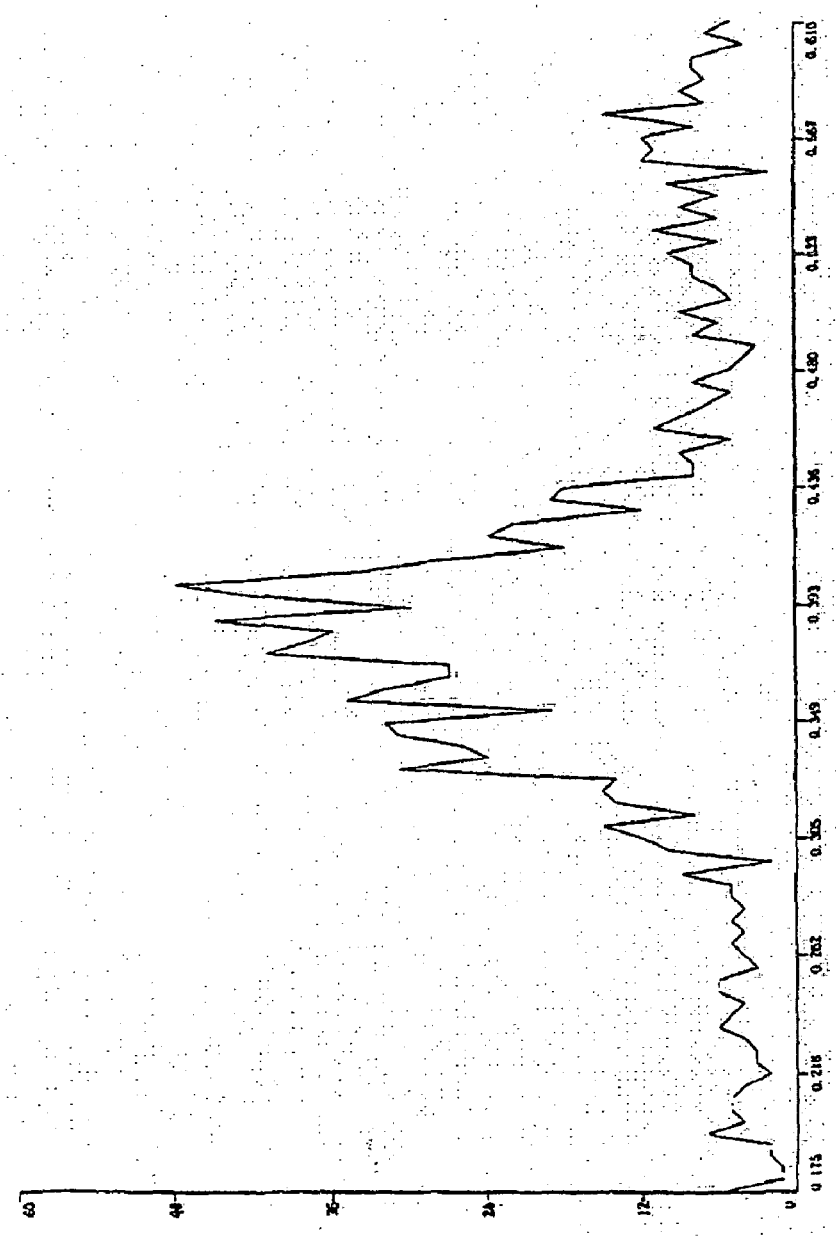
FIG. 11 is a diffraction pattern for the central part in a magnesium alloy work piece in a thickness of 25 mm.

In a second embodiment, as shown in FIG. 9, the device and method used in this embodiment are identical to those used in the first embodiment, with the difference in parameter selection: in this embodiment, WK$\alpha$ radiation is used, the tube voltage is 280 KV, the tube current is 3 mA, the distance from the center of the goniometer circle to the radiation detector is 220 mm±1.0, a NaI scintillation counter 6 is connected to the multi-channel energy analyzer 9, the collimator entrance diaphragm is a round-aperture collimator entrance diaphragm in an inner diameter of 2 mm±0.1 and a length of 120 mm±0.5 length, a round-aperture collimator entrance diaphragm in an inner diameter of 0.5 mm±0.1 and a length of 120 mm±0.5 is used for the position-restricting receiving slit, and the NaI scintillation counter 6 is shielded with an 8 mm±0.1 thick lead sheet. After the optical path is conditioned, a magnesium alloy casting 3 in a thickness of 25 mm±0.5 is placed on the table 4. The table 4 is adjusted so that the center of the magnesium alloy casting 3 is located in the center of the circle of the goniometer. The position indicated by the dotted line shown in FIG. 9 is an actual position of the magnesium alloy casting 3; in that case, the center of the circle of the goniometer is located inside of the magnesium alloy casting 3 with a distance of 12.5 mm±0.1 to the surface of the casting. The scan range 2$\theta$ is 2-10°, the step length of scan is 0.05°, and the measurement is performed for 10 s at each step. An obtained X-ray diffraction pattern is shown in FIG. 11.

In a third embodiment, the device and method used in this embodiment are identical to those used in the first embodiment, with the difference in parameter selection: in this embodiment, WK$\alpha$ radiation is used, the tube voltage is 320 KV, the tube current is 6 mA, the distance from the center of the goniometer circle to the radiation detector is 500 mm±1.0, a NaI scintillation counter 6 is connected to the multi-channel energy analyzer 9, the collimator entrance diaphragm is a round-aperture collimator entrance diaphragm in an inner diameter of 1 mm±0.1 and a length of 150 mm±0.5, a round-aperture collimator entrance diaphragm in an inner diameter of 0.8 mm±0.1 and a length of 120 mm±0.5 is used for the position-restricting receiving slit, and the NaI scintillation counter 6 is shielded with a 10 mm±0.1 thick lead sheet. After the optical path is conditioned, the work piece 3 is placed on the table 4. The table 4 is adjusted so that the center of the work piece 3 is located at the center of the circle of the goniometer; in that case, the center of the circle of the goniometer is located inside of the work piece 3. The scan range 2$\theta$ is 2-10°, the step length of scan is 0.05°, and the measurement is performed for 10 s at each step.

Though the invention is disclosed in the embodiments as above, it should be noted that those embodiments do not constitute any limitation to the invention. Any variations conceivable by those skilled in the art shall fall into the scope of the invention.

What is claimed is:

1. A short-wavelength X-ray diffraction measuring device, comprising an X-ray tube, an entrance diaphragm, a table, a goniometer, a detector, and an energy analyzer; wherein, the X-ray tube and the detector are located at two sides of the table, respectively, so that the X-ray tube and the detector are also located at two sides of a work piece placed on the table, respectively, and the detector receives short-wavelength X-rays diffracted by and transmitted through the work piece;
   wherein the table with the work piece placed thereon is translatable in X, Y, Z three dimensions, rotatable around a rotating axis of the goniometer to an angle $\Psi$, or movable in X, Y, Z three dimensions and to an angle $\Psi$ in a cooperative manner, so that different parts of the work piece can be measured; and
   wherein, during the measurement, the detector is scanned within a scan range 2$\theta$.

2. The short-wavelength X-ray diffraction measuring device according to claim 1, wherein, the entrance diaphragm is a collimator entrance diaphragm, comprising: a round-aperture collimator entrance diaphragm or a rectangular-aperture collimator entrance diaphragm.

3. The short-wavelength X-ray diffraction measuring device according to claim 2, wherein, the collimator entrance diaphragm is mainly made of barrier material comprising Pb or a heavy metal with a stronger X-ray absorption capability than Pb.

4. The short-wavelength X-ray diffraction measuring device according to claim 2, wherein, the round-aperture collimator entrance diaphragm is in an inner diameter of 0.1-2 mm and a length of 50-200 mm; the rectangular-aperture collimator entrance diaphragm is composed of two or more diaphragms, which are parallel to each other in the same direction and the center lines of which coincide with each other; the barrier material for each diaphragm is in a thickness of $\geq$4 mm the spacing between the diaphragms is 20-200 mm; an inner aperture of each diaphragm is of (1-4)×(0.1-

0.8)mm; the total thickness of the barrier materials for the entire rectangular-aperture collimator entrance diaphragm is not less than 15 mm.

5. The short-wavelength X-ray diffraction measuring device according to claim 1, further comprising a receiving slit located between the table and the detector.

6. The short-wavelength X-ray diffraction measuring device according to claim 5, wherein, the receiving slit is a parallel position-restricting receiving slit or a tapered position-restricting receiving slit configured to permit only diffracted X-rays from a measured part of the work piece entering into the detector, and shield scattered X-rays or diffracted rays from other parts of the work piece from entering into the detector.

7. The short-wavelength X-ray diffraction measuring device according to claim 6, wherein, the receiving slit is mainly made of barrier material comprising Pb or another heavy metal with a stronger X-ray absorption capability than Pb.

8. The short-wavelength X-ray diffraction measuring device according to claim 6, wherein, the taper of the tapered position-restricting receiving slit depends on a limited angle detectable by the position-sensitive detector; a casing of the tapered position-restricting receiving slit is covered with a lead sheet in a thickness greater than 2 mm, and inlaid with 3-10 tungsten or molybdenum plates that divide the taper of the tapered position-restricting receiving slit evenly; the dimension of a larger opening of the slit matches the effective dimension of the position-sensitive detector; the tapered surface of the tapered position-restricting receiving slit intersects with the extension of the inlaid tungsten or molybdenum plates at the rotating axis of the goniometer; the center line of the tapered position-restricting receiving slit intersects with the center line of the lined tungsten or molybdenum plate at the center of the circle of the goniometer; the tapered position-restricting receiving slit and the position-sensitive detector are movable in an cooperative manner; if a position-sensitive detector is used to collect a diffraction pattern, a tapered position-restricting receiving slit is used as the receiving slit.

9. The short-wavelength X-ray diffraction measuring method according to claim 8, wherein, the receiving slit is fixed to the position-sensitive detector.

10. The short-wavelength X-ray diffraction measuring device according to claim 5, wherein, the detector comprises a single-point radiation detector or a one-dimensional semiconductor detector array.

11. The short-wavelength X-ray diffraction measuring device according to claim 10, wherein, the one-dimensional semiconductor detector array is a position sensitive detector.

12. The short-wavelength X-ray diffraction measuring device according to claim 10, wherein, the distance from the X-ray tube to the center of the circle of the goniometer is equal or not equal to the distance from the detector to the center of the circle of the goniometer, and is adjustable; the distance from the center of the circle of the goniometer to the detector is 200-800 mm; the center of the circle of the goniometer is an intersection point between the rotating axis of the goniometer and a rotation plane of the detector; an incident X-ray is in the rotation plane of the detector and passes through the center of the circle of the goniometer; a part of the work piece at the center of the circle of the goniometer is a measured part; if the single-point radiation detector is used to scan and collect a diffraction pattern, a round-aperture collimator entrance diaphragm or a rectangular-aperture collimator entrance diaphragm is used for the parallel position-restricting receiving slit.

13. The short-wavelength X-ray diffraction measuring device according to claim 12, wherein, the round-aperture collimator entrance diaphragm is in an inner diameter of 0.1-2 mm and a length of 50-200 mm; the rectangular-aperture collimator entrance diaphragm is composed of two or more diaphragms, which are parallel to each other in the same direction and the center lines of which coincide with each other; the barrier material for each diaphragm is in a thickness of $\geq 4$ mm; the spacing between the diaphragms is 20-200 mm; an inner aperture of each diaphragm is of (1-4)×(0.1-0.8)mm; the total thickness of the barrier materials for the entire rectangular-aperture collimator entrance diaphragm is not less than 15 mm.

14. The short-wavelength X-ray diffraction measuring device according to claim 5, wherein, the receiving slit and the detector are fixed to the goniometer and synchronously rotatable around a measured part in the work piece placed on the table, the measured part is on the rotating axis of the goniometer; the goniometer is fixed to a platform; the table is fixed to the goniometer or the platform; the X-ray tube is fixed to the goniometer or the platform; the entrance diaphragm is fixed to the goniometer, the platform, or a clamp for the X-ray tube; an exit of the diaphragm is on or within the circumference of the goniometer.

15. The short-wavelength X-ray diffraction measuring device according to claim 5, wherein, the detector is packaged by a lead sheet in a thickness greater than 2 mm or another heavy metal sheet with a stronger X-ray absorption capability than Pb to shield X-rays, leaving only a window over against the receiving slit and a pinhole for leading out electric wires.

16. The short-wavelength X-ray diffraction measuring device according to claim 5, wherein, an anode target of the X-ray tube is made of a heavy metal material; the tube voltage is 120-350 KV, adjustable steplessly.

17. The short-wavelength X-ray diffraction measuring device according to claim 16, wherein, the heavy metal material is W, Au, or Ag.

18. The short-wavelength X-ray diffraction measuring device according to claim 5, wherein, the table is translatable in X, Y, and Z three dimensions or rotatable around the rotating axis of the goniometer under the control of a computer; the energy analyzer outputs signals to the computer.

19. The short-wavelength X-ray diffraction measuring device according to claim 5, wherein, the energy analyzer picks up directly the characteristic diffraction X-ray entering into the detector.

20. The short-wavelength X-ray diffraction measuring device according to claim 19, wherein, the energy analyzer is a single-channel energy analyzer or a multi-channel energy analyzer.

21. The short-wavelength X-ray diffraction measuring device according to claim 1, wherein, an anode target of the X-ray tube is made of a heavy metal material; the tube voltage is 120-350 KV, adjustable steplessly.

22. The short-wavelength X-ray diffraction measuring device according to claim 21, wherein, the heavy metal material is W, Au, or Ag.

23. The short-wavelength X-ray diffraction measuring device according to claim 1, wherein, the table is translatable in X, Y, and Z three dimensions or rotatable around the rotating axis of the goniometer under the control of a computer; the energy analyzer outputs signals to the computer.

24. The short-wavelength X-ray diffraction measuring device according to claim 1, wherein, the detector comprises a single-point radiation detector or a one-dimensional semiconductor detector array.

25. The short-wavelength X-ray diffraction measuring device according to claim 23, wherein, the one-dimensional semiconductor detector array is a position sensitive detector.

26. The short-wavelength X-ray diffraction measuring device according to claim 1, wherein, the energy analyzer picks up directly the characteristic diffraction X-ray entering into the detector.

27. The short-wavelength X-ray diffraction measuring device according to claim 26, wherein, the energy analyzer is a single-channel energy analyzer or a multi-channel energy analyzer.

28. A short-wavelength X-ray diffraction measuring method, comprising the following steps:
   1) placing a detector and an X-ray tube at two sides of a table, respectively, so that the detector can receive short-wavelength X-rays radiated from the X-ray tube and diffracted by and transmitted through a work piece placed on the table;
   2) selecting radiation and diffraction test parameters, including tube voltage, tube current, entrance diaphragm and receiving slit system, energy analyzer, and the distance from the center of the circle of a goniometer to the detector;
   3) placing a measured part of the work piece at the center of the circle of the goniometer;
   4) measuring a diffraction pattern;
   5) translating the table with the work piece placed thereon in at least one of X, Y, Z three dimensions, rotating the table with the work piece placed thereon around a rotating axis of the goniometer to an angle $\Psi$, or moving the table with the work piece placed thereon in at least one of X, Y, Z three dimensions and to an angle $\Psi$ in a cooperative manner, to measure a diffraction pattern for a different part of the work piece from the measured part, and
   wherein, during the measurement, the detector is scanned within a scan range $2\theta$.

29. The short-wavelength X-ray diffraction measuring method according to claim 28, wherein, selecting radiation and diffraction test parameters comprises selecting short-wavelength characteristic X-rays.

30. The short-wavelength X-ray diffraction measuring method according to claim 29, wherein, the energy analyzer picks up directly the characteristic diffraction X-ray entering into the detector.

31. The short-wavelength X-ray diffraction measuring method according to claim 30, wherein, the energy analyzer is a single-channel energy analyzer or a multi-channel energy analyzer.

32. The short-wavelength X-ray diffraction measuring method according to claim 28, wherein, the receiving slit permits only diffracted X-rays from the measured part of the work piece entering into the detector but shields scattered X-rays or diffracted rays from other parts of the work piece from entering into the detector, and comprises a parallel position-restricting receiving slit when a single-point radiation detector is used to scan and collect the diffraction pattern, or a tapered position-restricting receiving slit when a One-dimensional detector array is used to collect the diffraction pattern.

33. The short-wavelength X-ray diffraction measuring method according to claim 32, wherein, the energy analyzer picks up directly the characteristic diffraction X-ray entering into the detector.

34. The short-wavelength X-ray diffraction measuring method according to claim 33, wherein, the energy analyzer is a single-channel energy analyzer or a multi-channel energy analyzer.

35. The short-wavelength X-ray diffraction measuring method according to claim 32, wherein, the one-dimensional detector array is a position sensitive detector.

36. The short-wavelength X-ray diffraction measuring method according to claim 35, wherein, the energy analyzer picks up directly the characteristic diffraction X-ray entering into the detector.

37. The short-wavelength X-ray diffraction measuring method according to claim 36, wherein, the energy analyzer is a single-channel energy analyzer or a multi-channel energy analyzer.

38. The short-wavelength X-ray diffraction measuring method according to claim 28, wherein, the entrance diaphragm is a collimator entrance diaphragm, comprising: a round-aperture collimator entrance diaphragm or a rectangular-aperture collimator entrance diaphragm.

39. The short-wavelength X-ray diffraction measuring method according to claim 28, wherein, the detector is packaged by a lead sheet in a thickness greater than 2 mm or another heavy metal sheet with a stronger X-ray absorption capability than Pb to shield X-rays, leaving only a window over against the receiving slit and a pinhole for leading out electric wires.

40. The short-wavelength X-ray diffraction measuring method according to claim 28, wherein, the measured part in the work piece is placed at the center of the goniometer circle under the control of a computer; the measured part is any part on the surface of the work piece or inside of the work piece within a measurable thickness range.

41. The short-wavelength X-ray diffraction measuring method according to claim 28, wherein, during measurement of the diffraction pattern, the measured work piece is translated along with the table in X, Y, Z three dimensions at a step length of 0.1-2 mm and/or rotated around a rotating axis of the goniometer as required under the control of a computer, so as to measure the diffraction pattern at any part in the work piece or at any rotated angle around the rotating axis of the goniometer.

42. The short-wavelength X-ray diffraction measuring method according to claim 28, wherein, the energy analyzer picks up directly the characteristic diffraction X-ray entering into the detector.

43. The short-wavelength X-ray diffraction measuring method according to claim 42, wherein, the energy analyzer is a single-channel energy analyzer or a multi-channel energy analyzer.

44. The short-wavelength X-ray diffraction measuring method according to claim 28, further comprising processing the measured data by a computer to obtain parameters at different parts, comprising phase parameters and residual stress parameters, and their distribution in the work piece.

\* \* \* \* \*